US007845551B2

(12) United States Patent
Helmin et al.

(10) Patent No.: US 7,845,551 B2
(45) Date of Patent: *Dec. 7, 2010

(54) SYSTEM AND METHOD FOR COMPARING DRUG PRODUCT INFORMATION

(75) Inventors: Robert P. Helmin, Blue Island, IL (US); William R. Magruder, Western Springs, IL (US)

(73) Assignee: Global Healthcare Exchange, LLC, Westminster, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/547,796

(22) Filed: Aug. 26, 2009

(65) Prior Publication Data

US 2009/0314832 A1   Dec. 24, 2009

Related U.S. Application Data

(63) Continuation of application No. 11/537,427, filed on Sep. 29, 2006, now Pat. No. 7,597,247.

(51) Int. Cl.
*G06F 17/00* (2006.01)
(52) U.S. Cl. .......................................... 235/375; 705/2
(58) Field of Classification Search .................. 235/375, 235/385
See application file for complete search history.

(56) References Cited

U.S. PATENT DOCUMENTS

| | | | | | |
|---|---|---|---|---|---|
| 4,918,604 | A | * | 4/1990 | Baum | 221/5 |
| 5,597,995 | A | * | 1/1997 | Williams et al. | 235/375 |
| 5,713,487 | A | * | 2/1998 | Coughlin | 221/2 |
| 5,833,599 | A | * | 11/1998 | Schrier et al. | 600/300 |
| 7,006,893 | B2 | * | 2/2006 | Hart et al. | 700/235 |
| 7,317,967 | B2 | * | 1/2008 | DiGianfilippo et al. | 700/265 |
| 7,505,917 | B2 | * | 3/2009 | Howe et al. | 705/2 |
| 2002/0002473 | A1 | * | 1/2002 | Schrier et al. | 705/3 |
| 2003/0055685 | A1 | * | 3/2003 | Cobb et al. | 705/3 |
| 2003/0135388 | A1 | * | 7/2003 | Martucci et al. | 705/2 |
| 2003/0174326 | A1 | * | 9/2003 | Rzasa et al. | 356/326 |
| 2003/0216831 | A1 | * | 11/2003 | Hart et al. | 700/235 |
| 2004/0107117 | A1 | * | 6/2004 | Denny | 705/2 |
| 2004/0158349 | A1 | * | 8/2004 | Bonney et al. | 700/231 |
| 2004/0207842 | A1 | * | 10/2004 | Rzasa et al. | 356/328 |
| 2004/0243434 | A1 | * | 12/2004 | Peterka et al. | 705/2 |
| 2005/0086008 | A1 | * | 4/2005 | DiGianfilippo et al. | 702/19 |
| 2005/0240305 | A1 | * | 10/2005 | Bogash et al. | 700/242 |
| 2006/0089858 | A1 | * | 4/2006 | Ling | 705/2 |
| 2006/0095300 | A1 | * | 5/2006 | Schrier et al. | 705/3 |
| 2006/0098193 | A1 | * | 5/2006 | Rzasa et al. | 356/300 |

(Continued)

OTHER PUBLICATIONS

Office Action U.S. Appl. No. 11/537,427 dated Oct. 17, 2008.

(Continued)

*Primary Examiner*—Daniel A Hess
*Assistant Examiner*—Paultep Savusdiphol
(74) *Attorney, Agent, or Firm*—Snell & Wilmer L.L.P.

(57) ABSTRACT

A system and method for comparing vast amounts of drug product information at granular levels is provided. This comparison is facilitated by the creation of a unique key that maintains the integrity of the comparison system. The unique key may contain a therapeutic class identifier, a clinical formulation identifier, an additional detail identifier, a package equivalent size identifier, a unit dose identifier, and a package quantity identifier.

15 Claims, 2 Drawing Sheets

U.S. PATENT DOCUMENTS

2006/0259326 A1* 11/2006 Ambekar et al. ............... 705/2
2007/0050275 A1* 3/2007 Hunsicker ................... 705/35
2007/0214014 A1* 9/2007 Suwalski et al. .............. 705/3
2007/0233516 A1* 10/2007 Howe et al. ................... 705/2
2007/0250341 A1* 10/2007 Howe et al. ................... 705/2

OTHER PUBLICATIONS

Final Office Action U.S. Appl. No. 11/537,427 dated Apr. 15, 2009.
Advisory Action U.S. Appl. No. 11/537,427 dated Jul. 16, 2009.
Notice of Allowance U.S. Appl. No. 11/537,427 dated Aug. 7, 2009.

* cited by examiner

SYSTEM AND METHOD FOR COMPARING DRUG PRODUCT INFORMATION

CROSS REFERENCE TO RELATED APPLICATIONS

This application claims priority to, and is a continuation of, U.S. patent application Ser. No. 11/537,427, filed Sep. 29, 2006 and entitled "System and Method for Comparing Drug Product Information." This application hereby incorporates by reference this prior application in its entirety.

FIELD OF INVENTION

The present invention is generally related to supply chain management in the pharmaceutical industry, and more particularly, to the comparison, storage, management and ordering of pharmaceutical and associated product information.

BACKGROUND OF THE INVENTION

In general, the management and ordering of pharmaceuticals for an organization, such as a hospital pharmacy department, is an expensive endeavor. Oftentimes, pharmacy departments have some of the highest expenses in a hospital. As such, in today's cost sensitive health environment, healthcare organizations are constantly challenging their pharmacy departments to reduce costs and spending.

While many factors contribute to high administrative costs, one contributing factor is the number of drugs an organization needs to track and/or order. In an effort for a health organization to better control its costs, the organization usually needs to access accurate pricing quotes for drugs offered through multiple manufacturers. However, the same or similar drug may be offered in many different package sizes, routes of administration, strength, dosage forms and the like. Adding to this complexity, the generic drug market is expanding at an exponential rate with new companies producing generically equivalent products. As such, a particular drug may be known by many different names such as a trademarked name of a drug or its generic or chemical name.

Due to these complexities, many healthcare providers utilize supply chain management companies that have created systems which aggregate vast amounts of drug information and provide this information to healthcare providers. Providers use these various systems to aid with the management of drug information and supply contracts associated with these drugs. By utilizing this information, healthcare providers are able to better control costs, increase their negotiating power with drug suppliers during contract negotiations, increase the accuracy of their orders, and facilitate quicker payment resolution. However, due to differences in product naming conventions, manufacturer's product descriptions, strengths, and dosages and the like amongst the same or similar active ingredients of a drug, much of the aggregated data cannot be easily cross-referenced according to the generic name across various manufacturers that produce a drug. For example, oftentimes a drug manufacturer will sell its trademarked brand of drug without ever referring to the active ingredient or generic name of the drug. As such, it is difficult for a healthcare provider to obtain the best contract purchase price or to reconcile inventory projections and usage.

Thus, a longtime need exists for a system and method that captures and organizes drug product information at the generic level so that a comparison can be made across various manufacturers.

SUMMARY OF THE INVENTION

The present invention includes systems and methods for comparing and storing drug product information. An exemplary system for drug product information comparison comprises one or more data feeds, a processing engine, a database, and a reporting engine. Drug product information is gleaned from various data feeds comprising data describing drugs and their characteristics, manufacturers and wholesalers, contract information, membership information and/or the like. The processing engine parses the incoming data feeds and assembles a unique key so that the data feed information can be inserted into the database while maintaining data integrity. The unique key may contain a therapeutic class identifier, a clinical formulation identifier, an additional detail identifier, a package equivalent size identifier, a unit dose identifier, and a package quantity identifier. The reporting engine enables access by a user such that the user can run various reports.

An exemplary method includes the steps of parsing incoming data feed(s) of drug product information, assembling unique keys based on such information, storing unique keys and drug product information in a database, receiving report criteria, retrieving report data from a database based on the criteria and using the unique key, and outputting the report data. The reporting engine may contain pre-determined reports to facilitate quick comparisons and expedited reporting. Report data may be output first at a summary level according to the most often used criteria, along with the ability to retrieve more detailed data by selecting elements on the summary report. In that regard, the present invention enables vast amounts of drug product information to be compared and cross-referenced at generic level.

DESCRIPTION OF THE FIGURES

These and other features, aspects, and advantages of the invention may best be understood by reference to the following description taken in conjunction with the accompanying drawings in which like numerals represent like elements.

DETAILED DESCRIPTION OF EXEMPLARY EMBODIMENTS

Figure 1:
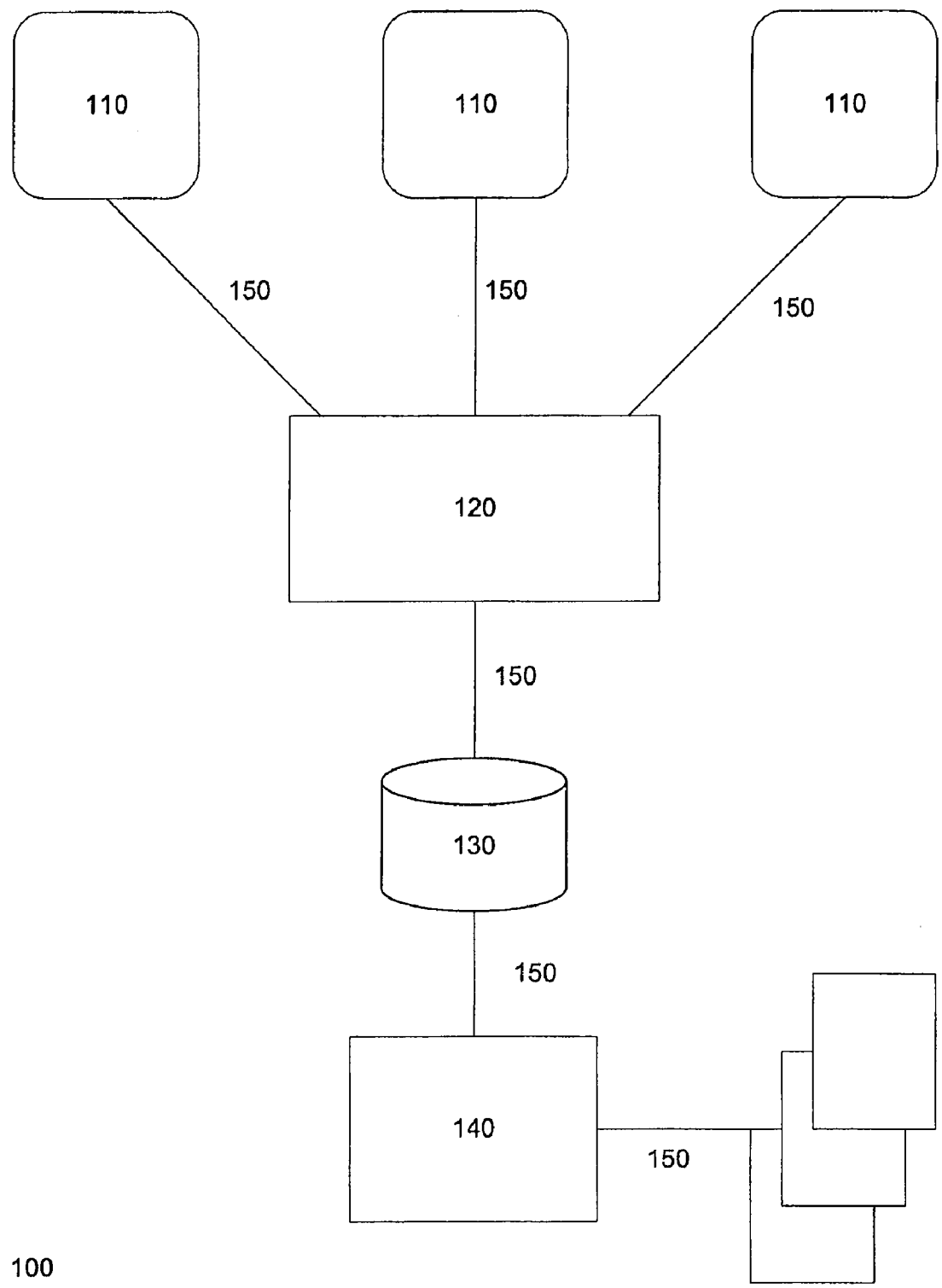
FIG. 1 shows an exemplary drug product information comparison system in accordance with an exemplary embodiment of the present invention; and, FIG. 2 shows a flow chart of an exemplary method for comparing drug product information in accordance with an exemplary embodiment of the present invention.

The present invention facilitates the storage, comparison and cross-referencing of drug product information at a generic level. The invention includes a system and method for comparing drug product information, using small fragments of data, without the need to know manufacturer specific information, the NDC (National Drug Code) designation, or trade name for each drug. Drug product information includes, for example, any information describing drugs and their ingredients and characteristics, manufacturers and wholesalers, contract information, membership information or any information typically utilized in the supply chain management of the pharmaceutical and healthcare industry. For example, many similar drugs contain the same active ingredients, but have different attributes such as, for example, inactive ingredients, dosages, strengths, route of administration, and the like. In order to facilitate cost and spending reductions, the invention enables health care organizations to compare the various drugs at a granular level.

Based on such a comparison, purchase history, contract compliance, request for quotations and/or various other management functions may be performed. For example, suitable drug substitutes (e.g., generic vs. trademarked drug) or identification of a competitive manufacturer may be found. For example, drug manufacturer A may sell a drug under a trademark in pill form containing 20 MG of active ingredient per pill in bottles of 50 pills. Drug manufacturer B may sell the same drug under a different trademark containing 20 MG of active ingredient per pill but in bottles of 100 pills. Drug manufacturer A may price the drug so that the cost per pill is more than drug manufacturer B's 20 MG pill. The present invention enables the comparison of the two drugs at a level granular enough so that a healthcare provider could identify the lower cost per pill, and employ cost saving measures to use the less expensive manufacturer B product.

Moreover, a healthcare organization or a manufacturer may use the systems and methods of the present invention in contract bidding. Drug product information may be summed by a number of characteristics valuable in the contract bidding process. For example, a bidder may generate reports that reveal manufacturer market share according to the product(s) contained in the request for quotations (RFQ). The bidder may analyze whether a particular contract is suitable should the contract be awarded to the bidder. The healthcare organization who originated the RFQ may use the systems and methods of the present invention to group and compare the responses. For example, the responses may be grouped according to generic name, route of administration, dosage form, strength, package type, package size, and/or package quantity regardless of the manufacturer. The response may be further sorted according to bid cost (e.g., lowest to highest bid price). In doing so, a healthcare organization can quickly organize bid responses and select the appropriate bid for its needs.

Because the data that describes the various attributes of the various drug products is maintained by separate entities and described differently within each entity, the invention facilitates maintaining integrity across the disparate data sources. The integrity is facilitated by the creation of a unique key, wherein the unique key, in one embodiment, is dependent partially on the data sources, and the key contains an identifier independent of any one particular data source. Because this integrity is maintained, drug product information comparisons can be made with increased specificity and in a definitive manner. For example, if a particular healthcare organization seeks information for dye free pediatric liquid medications, reports are generated that do not contain medications that incorporate a dye. Thus, as will become apparent from the following descriptions, the systems and methods of the invention facilitate comparing vast amounts of drug product information based on a unique key that enables cross-referencing across such drug product information.

For the sake of brevity, conventional data networking, application development and other functional aspects of the systems (and components of the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical system.

The invention may be described herein in terms of functional block components, optional selections and various processing steps. It should be appreciated that such functional blocks may be realized by any number of hardware and/or software components configured to perform the specified functions. For example, the invention may employ various integrated circuit components, e.g., memory elements, processing elements, logic elements, look-up tables, and the like, which may carry out a variety of functions under the control of one or more microprocessors or other control devices.

Similarly, the software elements of the invention may be implemented with any programming, scripting language or web service protocols such as C, C++, Macromedia Cold Fusion, Microsoft Active Server Pages, Java, COBOL, assembler, PERL, Visual Basic, SQL Stored Procedures, extensible markup language (XML), with the various algorithms being implemented with any combination of data structures, objects, processes, routines or other programming elements. Further, it should be noted that the invention may employ any number of conventional techniques for data transmission, signaling, data processing, network control, and the like, e.g., TCP/IP, IPX, Appletalk, IP-v6, NetBIOS, OSI or any number of existing or future protocols. For additional information on communication systems, network programming, web services, and security, refer to Gilber Held, "Understanding Data Communications," (1996); Dilip Naik, "Internet Standards and Protocols," (1998); and Java 2 Complete, various authors (Sybex 1999); the Object Management Group website at http://.omg.org; the Sun Microsystems JAVA web site at http://www.sunjava.com; the Universal Description, Discovery, and Integration Organization at http://www.uddi.org; and "Cryptography & Network Security: Principles & Practice" by William Stalling, published by Prentice Hall; all of which are incorporated by reference.

FIG. 1 illustrates, in block format, an exemplary drug product information comparison system 100 of the invention. In one embodiment, drug product information comparison system comprises one or more data feeds 110, a processing engine 120, a database 130, and a reporting engine 140. The system components communicate over one or more networks 150, using any of the protocols described herein or are suited to the particular component and communication.

Data feed 110 may include any collection of data or information suitable for processing by the system 100. Data feed 110 may be internal or external to the system 100 and be provided in various formats such as, for example, ASCII or XML. Data feed 110 will contain records representing a collection of fields that may describe any number of aspects of the information to be included in the system 100. Each record may have a unique attribute, such as a number, field, or set of fields) which may uniquely identify the record within the particular data feed. Multiple data feeds may be utilized to gather information for a variety of sources. In its exemplary embodiments, the information contained within the data feeds describe various drug product information attributes, for example, drug composition, wholesaler information, national drug code information (e.g., from the National Drug Code Directory provided by the U.S. Food and Drug Administration), contract information, and/or membership information (e.g., whether a particular drug belongs in a particular health plan, or whether a particular organization belongs in a membership-only purchasing network).

Processing engine 120 includes any hardware and/or software suitably configured to parse incoming data feed(s) 110 and to assemble a unique key enabling comparison and cross-referencing of drug product information at a generic level. In general, processing engine 120 is implemented as a combination of databases, servers, and application software that are configured so that the data feed(s) 110 pass through processing engine 120 to be parsed, and so that drug product information and the unique key can be input into database 130.

Operation of processing engines to running parsing, assembly, and database management functions is known and will not be described in detail. In various embodiments, it should be appreciated that, although not shown or described, additional connections, links and/or adapter interfaces may occur between components of the system such as connections to a wireless base station, web translation server, router, and/or a coordinator system to drive routing within the system. In this manner, processing engine 120 may include multiple networks capable of communication between networks and other components of the system.

Database 130 may be any type of database, such as relational, hierarchical, object-oriented, and/or the like. Common database products that may be used to implement the databases include DB2 by IBM (White Plains, N.Y.), any of the database products available from Oracle Corporation (Redwood Shores, Calif.), Microsoft Access by Microsoft Corporation (Redmond, Wash.), or any other database product. Database 130 may be organized in any suitable manner, including as data tables or lookup tables. Association of certain data may be accomplished through any data association technique known and practiced in the art. For example, the association may be accomplished either manually or automatically. Automatic association techniques may include, for example, a database search, a database merge, GREP, AGREP, SQL, and/or the like. The association step may be accomplished by a database merge function, for example, using a "key field" in each of the manufacturer and retailer data tables. A "key field" partitions the database according to the high-level class of objects defined by the key field. For example, a certain class may be designated as a key field in both the first data table and the second data table, and the two data tables may then be merged on the basis of the class data in the key field. In this embodiment, the data corresponding to the key field in each of the merged data tables is preferably the same. However, data tables having similar, though not identical, data in the key fields may also be merged by using AGREP, for example.

The data set annotation may also be used for other types of status information as well as various other purposes. For example, the data set annotation may include security information establishing access levels. The access levels may, for example, be configured to permit only certain individuals, levels of employees, companies, or other entities to access data sets, or to permit access to specific data sets based on the transaction, health care institution, user or the like. Furthermore, the security information may restrict/permit only certain actions such as accessing, modifying, and/or deleting data sets. In one example, the data set annotation indicates that only the data set owner or the user are permitted to delete a data set, various identified users may be permitted to access the data set for reading, and others are altogether excluded from accessing the data set. However, other access restriction parameters may also be used allowing various entities to access a data set with various permission levels as appropriate.

One skilled in the art will also appreciate that, for security reasons, any databases, systems, devices, servers or other components of the system may consist of any combination thereof at a single location or at multiple locations, wherein each database or system includes any of various suitable security features, such as firewalls, access codes, encryption, decryption, compression, decompression, and/or the like.

A reporting engine 140 includes any hardware and/or software suitably configured to accept input through an interface, query the database 130, and retrieve and output results of the query from database 130. In general, reporting engine 140 is implemented as a combination of databases, servers, and application software that are configured so that a user (defined as any human entity or electronic means such as a software or hardware agent) may access drug product information through a variety of interface and/or networks. Various reporting engines and their operational characteristics are known and will not be described in detail. As such, it should be appreciated that, although not shown or described, additional connections, links, hardware, software, databases, and/or interfaces and the like may be used to produce various reports with respect to the system. In yet other embodiments, the reporting engine 140 is configured to provide audit trails sufficient to meet any regulatory or auditing requirements with respect to the hardware, software, or data employed in the system.

Figure 2:
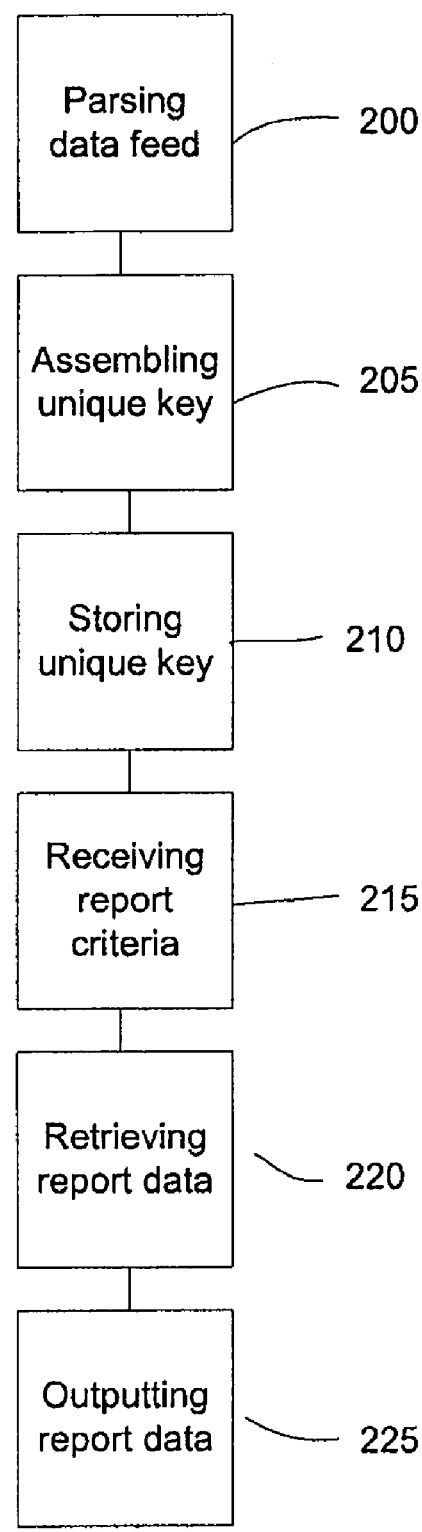

In accordance with the present invention and with reference to FIG. 2, an exemplary method includes, in general, parsing incoming data feed(s) of drug product information (step 200), assembling unique keys based on such information (step 205), storing the unique keys in a database (step 210), receiving report criteria (step 215), retrieving report data from a database based on the criteria and using a unique key (step 220), and outputting the report data (step 225).

In various embodiments, parsing incoming data feed(s) (step 200) includes selecting those parts of the data feed which identify a particular attribute unique to the feed and creating an identifier. For example, a data feed may include the description and therapeutic class of a number of drug products. In this feed, each product may have been assigned a unique element (e.g., a number, field, or set of fields) by the originator of the data feed. The parsing function identifies the unique attribute (which would identify a record in the data feed) and notes it for later assembly. Identification of the unique attribute in a data feed may be pre-determined (e.g., one knows that the first four characters of a line in a data feed represent the unique attribute) or the parsing function may employ artificial intelligence designed to identify the unique attribute for each data feed. In various embodiments, some of the parsing functions may be performed by human intervention through a user interface. For example, human intervention may be needed to provide (i.e., insert into the data feed) a unique attribute for the particular data feed. Although an example has been provided describing a unique attribute in the data feed, there is no requirement that a particular attribute in any data feed be unique; rather, the records associated with data feed should simply be identified with certainty in the parsing process. Once the unique attribute is parsed, this attribute is considered the data feed identifier for the particular data feed.

After the parsing process, assembling unique keys based on data feed information (step 205) comprises assembling the parsed data feed identifiers into one key that uniquely identifies each drug product to be contained in database 130. In an exemplary embodiment, the data feed identifiers are concatenated together with an identifier not dependent on any data feed. However, any technique (e.g., data translation, use of cryptographic methods, etc.) that assembles identifiers into a unique key may be suitable.

In various embodiments, the unique key comprises a therapeutic class identifier; a clinical formulation identifier; an additional detail identifier; a billing unit identifier; a unit dose identifier; and a package size equivalent identifier. In exemplary embodiments, the length of the unique key is 25 characters.

In various embodiments, the therapeutic class identifier represents the list of ingredients in a particular drug formulation. The therapeutic class identifier identifies a unique combination of active ingredients in a particular drug product irrespective of the manufacturer, package size, dosage form, route of administration, or strength. The number may be of any length; however, in an exemplary embodiment, the length is six characters. For example, a therapeutic class identifier, 000222, may identify the unique set of active ingredients: guaifenesin, dextromethorphan hydrobromide, and pseudoephedrine. Another therapeutic class identifier, 000223, may identify the unique set of active ingredients: guaifenesin, dextromethorphan hydrobromide, and acetaminophen. In one embodiment, the therapeutic identifier does not contain inactive ingredients.

In various embodiments, a clinical formulation identifier represents a unique combination of the ingredient(s), the route of administration, the dosage form, and/or the strength for a generic drug formulation. In doing so, the clinical formulation identifier aggregates drug products that share the same or similar characteristics, but are marketed by multiple manufacturers. Unlike the therapeutic class identifier which only identifies active ingredients, the clinical formulation identifier comprises an identifier that represents the full list of ingredients in the particular drug formulation. The identifier also comprises the route of administration which describes the method by which a drug is administered (e.g., oral, injection, topical, etc.). The dosage form is represented by a code which describes the form of the generic formulation of the drug such as tablet, capsule, or the like. The strength is represented by a code which describes the drug's potency.

To facilitate comparison, each combination of ingredients, route of administration, dosage, and strength is uniquely identified. For example, a generic drug formulation containing fluoxetine may differ only in strength. A drug product containing fluoxetine, taken orally, in the form of a capsule, and in 10 MG strength may be assigned a clinical formulation identifier of 046213. A drug product containing fluoxetine, taken orally, in the form of a capsule, and in 20 MG strength may be assigned a clinical formulation identifier of 046214. The length of the clinical formulation identifier may be of any length; however, in an exemplary embodiment, the length is six characters.

In various embodiments, the additional detail identifier represents unique details about a particular drug product not captured with the other identifiers. If a particular drug product does not possess any additional details, this identifier is set to a null value or character. For example, a drug product may be described as sterile. In this case, the additional detail identifier may be set to 0041. Another product may be described as "sulfite free" for which the additional detail identifier is set to 0042. The value of the additional detail identifier will be unique across the complete set of additional details described in the system. The length of the additional detail identifier may be of any length; however, in an exemplary embodiment, the length is four characters.

In various embodiments, the package size equivalent identifier represents the package size ranges of a particular drug product. Minor variations in the volume of packaging are used across different manufacturers. For example, one manufacturer may label and fill a product with 31 mL of liquid, while another manufacturer may label and fill their product with 28 mL of liquid. In both cases, the active ingredients, and therefore the therapeutic benefits, are the same in both packages. However, to facilitate comparison of drug product information across manufacturers, the minor variations in packaging size must be normalized. As such, the actual package size is examined and associated with a standard package size equivalent. Table 1 shows a non-limiting sample of standard package sizes assigned to standard package size equivalents.

| Package Size Range | Package Size Equivalent | Description |
|---|---|---|
| 14.00 to 16.00 | 15.00 | 15 mL = ½ fl. oz. |
| 26.250 to 31.00 | 30.00 | 30 mL = 1 fl. oz. |
| 3500 to 4000 | 4000 | 4 gm = ⅛ oz |

In some cases, the package size range will not be able to be assigned a package size equivalent. In such cases, the package size equivalent identifier is given a default value or assigned the same value as the package size. The length of the package size equivalent identifier may be any length; however, in an exemplary embodiment, the length is four characters.

In various embodiments, the unit dose identifier represents whether a drug product contains separate unit doses or unit dose packaging, for example, blister packs. The unit dose identifier enables the identification of the drug from the time the drug leaves the manufacturer to the time a patient uses the drug. For example, a manufacturer may provide 100 tablets of a drug with each tablet in an individually sealed and fully labeled blisterpack. The blisterpack label may contain various information describing the drug such as, for example, trade name, generic name, strength, NDC designation, lot number, expiration date, manufacturer name and/or other information (e.g., bar coding). However, the unit dose identifier represents that each tablet is considered a unit dose. Without the identifier, the fact that unit doses exist would be lost. Consequently, the unit dose identifier is not applicable in the case of injectable drug products, suppositories, bulk containers or powder-based. As such, the unit dose identifier is assigned a null or default value. The length of the unit dose identifier may be any length; however, in an exemplary embodiment, the length is two characters. For example, the unit dose identifier for a drug product containing unit doses would be set to 01.

In various embodiments, the pack quantity identifier represents the number of units within a particular package. For example, one injectable dose of a drug may be packaged in a 2 mL vial. However, the manufacturer may package multiple vials in one box. So that the proper comparisons between all the attributes of the particular drug can be made, the number of vials in the package must be accounted for. As such, the package quantity identifier is assigned a unique number for the number of units in the package. For example, if a box contains 5 units, the package identifier is assigned 001; a box containing 25 units may be assigned a package quantity identifier 005. The identifier is unique among packages sizes so that once an identifier is assigned to a package quantity, this assignment remains unique. The length of the pack quantity identifier may be any length; however, in an exemplary embodiment, the length is three characters.

After assembly, storing the unique keys in a database (step 210) comprises inputting the unique keys and associated drug product information into the database for storage and retrieval by the reporting engine. Various database schemas may be utilized to efficiently store drug product information; however, in one embodiment, all drug product information is related through the unique key. In an exemplary embodiment, not all information contained in the data feed is saved after parsing. The parsing process may also include the deletion of extraneous data from the data feed before inclusion in the database.

In its embodiments, receiving report criteria (step 215) comprises a user inputting various report criteria through an interface, upon which the interface submits the criteria to the database. Access may be conducted directly through a human operator, or through automated software programs. As such, a user includes any and all agents that may access the reporting engine. In exemplary embodiments, access is achieved by a human operator through a web page.

Upon access, the user is presented with various reporting criteria to select from. For example, reporting criteria includes any field contained in the database. However, in an exemplary embodiment, most often used parameters may be presented to a user such as manufacturer name, drug name (e.g., generic name or trademark name), price ranges, national drug code number and the like, with other parameters selectable upon further browsing of the interface. The user may submit any number of reporting criteria through the interface. After selection of the reporting criteria, the user submits the criteria to the database.

In its embodiments, retrieving report data from a database based on the criteria and using a unique key (step 220) comprises the reporting engine creating an appropriate query and transmitting the query to the database. Any query language configured to the particular database system employed is suitable. In exemplary embodiments, the query comprises the unique key so that comparison and cross-referencing integrity is maintained. Furthermore, various reports may be "predetermined" such that queries may be assembled quickly without the need to repeat the selection of all desired criteria upon each access to the system.

In its embodiments, outputting the report data (step 225) comprises transmitting the data retrieved from the database to the reporting engine and finally to the user. Data may be displayed in any matter; however, in exemplary embodiments, summary data is displayed by most often used criteria such as manufacturer, drug product, or national drug code number. The user is able to select summary data elements (i.e., "drill down") to retrieve more specific and detailed data related to the element selected. In various embodiments, reports may be printed, saved to storage media, or otherwise manipulated for final consumption. An exemplary report includes grouping drug product information according to generic name, route of administration, dosage form, strength, package type, package size, and/or package quantity regardless of the manufacturer, trade name, or NDC designation. Another exemplary report includes grouping drug product information according to generic name, route of administration, dosage form, strength, and/or package type. Yet another exemplary report includes grouping drug product information according to NDC designation by manufacturer use, total use, and/or market share. Yet another exemplary report is grouping drug product information according to the price bid by a particular manufacturer in a contract bidding process.

As used herein, the term "network" shall include any electronic communications means which incorporates both hardware and software components of such. Communication among the systems may be accomplished through any suitable communication channels, such as, for example, a telephone network, an extranet, an intranet, Internet, point of interaction device (point of sale device, personal digital assistant (e.g., Palm Pilot®, Blackberry®), cellular phone, kiosk, etc.), online communications, satellite communications, offline communications, wireless communications, transponder communications, local area network (LAN), wide area network (WAN), networked or linked devices, keyboard, mouse and/or any suitable communication or data input modality. Moreover, the system may also be implemented using TCP/IP, IPX, Appletalk, IP-6, NetBIOS, OSI or any number of existing or future protocols. If the network is in the nature of a public network, such as the Internet, it may be advantageous to presume the network to be insecure and open to eavesdroppers. Specific information related to the protocols, standards, and application software utilized in connection with the Internet is generally known to those skilled in the art and, as such, need not be detailed herein. See, for example, Dilip Naik, Internet Standards and Protocols (1998); Java 2 Complete, various authors, (Sybex 1999); Deborah Ray and Eric Ray, Mastering HTML 4.0 (1997); and Loshin, TCP/IP Clearly Explained (1997) and David Gourley and Brian Totty, HTTP, The Definitive Guide (2002), the contents of which are hereby incorporated by reference.

The various system components may be independently, separately or collectively suitably coupled to network 150 via data links which includes, for example, a connection to an Internet Service Provider (ISP) over the local loop as is typically used in connection with standard modem communication, cable modem, Dish networks, ISDN, Digital Subscriber Line (DSL), or various wireless communication methods, see, e.g., Gilbert Held, Understanding Data Communications (1996), which is hereby incorporated by reference. Moreover, the system contemplates the use, sale or distribution of any goods, services or information over any network having similar functionality described herein.

As used herein, "transmit" may include sending electronic data from one system component to another over a network connection. Additionally, as used herein, "data" or "information" may include encompassing information such as commands, queries, files, data for storage, and the like in digital or any other form.

In various embodiments, user interface may include a web-compliant devices suitably capable of processing web pages and multimedia information (i.e., text, graphics, video and/or audio), and may include web-client software, an audio processor, a visual display, and/or an audio transducers. Web-compliant devices may be of a type capable of establishing a packet communication link via the Internet using a common protocol, e.g., Hyper-Text Transfer Protocol (HTTP), the operation of which is beyond the scope of this invention and will not be described in detail.

The various system components discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various databases used herein may include: client data; health care institution data; drug product data; safety data; manufacturer data and/or like data useful in the operation of the system. As those skilled in the art will appreciate, devices may include an operating system (e.g., Windows NT, 95/98/2000, OS2, UNIX, Linux, Solaris, MacOS, etc.) as well as various conventional support software and drivers typically associated with computers. The computer may include any suitable personal computer, network computer, workstation, minicomputer, mainframe or the like. User computer can be in a home or business environment with access to a network. In an exemplary embodiment, access is through a network or the Internet through a commercially-available web-browser software package.

The system contemplates uses in association with web services, utility computing, pervasive and individualized computing, security and identity solutions, autonomic computing, commodity computing, mobility and wireless solutions, open source, biometrics, grid computing and/or mesh computing.

The computing unit of the web client may be further equipped with an Internet browser connected to the Internet or an intranet using standard dial-up, cable, DSL or any other Internet protocol known in the art. Transactions originating at a web client may pass through a firewall in order to prevent unauthorized access from users of other networks.

Firewall may include any hardware and/or software suitably configured to protect components and/or enterprise computing resources from users of other networks. Further, a firewall may be configured to limit or restrict access to various systems and components behind the firewall for web clients connecting through a web server. Firewall may reside in varying configurations including Stateful Inspection, Proxy based and Packet Filtering among others. Firewall may be integrated within a web server or any other components or may further reside as a separate entity.

The components discussed herein may provide a suitable website or other Internet-based graphical user interface which is accessible by users. In one embodiment, the Microsoft Internet Information Server (IIS), Microsoft Transaction Server (MTS), and Microsoft SQL Server, are used in conjunction with the Microsoft operating system, Microsoft NT web server software, a Microsoft SQL Server database system, and a Microsoft Commerce Server. Additionally, components such as Access or Microsoft SQL Server, Oracle, Sybase, Informix MySQL, Interbase, etc., may be used to provide an Active Data Object (ADO) compliant database management system.

Any of the communications, inputs, storage, databases or displays discussed herein may be facilitated through a website having web pages. The term "web page" as it is used herein is not meant to limit the type of documents and applications that might be used to interact with the user. For example, a typical website might include, in addition to standard HTML documents, various forms, Java applets, JavaScript, active server pages (ASP), common gateway interface scripts (CGI), extensible markup language (XML), dynamic HTML, cascading style sheets (CSS), helper applications, plug-ins, and the like. A server may include a web service that receives a request from a web server, the request including a URL and an IP address. The web server retrieves the appropriate web pages and sends the data or applications for the web pages to the IP address. Web services are applications that are capable of interacting with other applications over a communications means, such as the internet. Web services are typically based on standards or protocols such as XML, SOAP, WSDL and UDDI. Web services methods are well known in the art, and are covered in many standard texts. See, e.g., Alex Nghiem, IT Web Services: A Roadmap for the Enterprise (2003), hereby incorporated by reference.

Practitioners will also appreciate that there are a number of methods for displaying data within a browser-based document. Data may be represented as standard text or within a fixed list, scrollable list, drop-down list, editable text field, fixed text field, pop-up window, and the like. Likewise, there are a number of methods available for modifying data in a web page such as, for example, free text entry using a keyboard, selection of menu items, check boxes, option boxes, and the like.

As will be appreciated by one of ordinary skill in the art, the system may be embodied as a customization of an existing system, an add-on product, upgraded software, a stand alone system, a distributed system, a method, a data processing system, a device for data processing, and/or a computer program product. Accordingly, the system may take the form of an entirely software embodiment, an entirely hardware embodiment, or an embodiment combining aspects of both software and hardware. Furthermore, the system may take the form of a computer program product on a computer-readable storage medium having computer-readable program code means embodied in the storage medium. Any suitable computer-readable storage medium may be utilized, including hard disks, CD-ROM, optical storage devices, magnetic storage devices, and/or the like.

These computer program instructions may be loaded onto a general purpose computer, special purpose computer, or other programmable data processing apparatus to produce a machine, such that the instructions that execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions. Further, illustrations of the process flows and the descriptions thereof may make reference to user windows, web pages, websites, web forms, prompts, etc. Practitioners will appreciate that the illustrated steps described herein may comprise in any number of configurations including the use of windows, web pages, web forms, popup windows, prompts and the like. It should be further appreciated that the multiple steps as illustrated and described may be combined into single web pages and/or windows but have been expanded for the sake of simplicity. In other cases, steps illustrated and described as single process steps may be separated into multiple web pages and/or windows but have been combined for simplicity.

Finally, it should be understood that various principles of the invention have been described in illustrative embodiments. However, many combinations and modifications of the above-described components, used in the practice of the invention, in addition to those not specifically described, may be varied and particularly adapted to specific environments and operating requirements without departing from those principles. Other variations and modifications of the present invention will be apparent to those of ordinary skill in the art, and it is the intent that such variations and modifications be covered.

What is claimed is:

1. A system comprising:
a network interface communicating with a memory;
the memory communicating with a processor;
and the processor, when executing a computer program, is configured to:
receive a first data feed and a second data feed;
parse the first data feed into first data and the second data feed into second data;
assemble a first unique key by transforming the first data, wherein the first unique key comprises at least one of a package quantity identifier, a therapeutic class identifier, a clinical formulation identifier, an additional detail identifier, a package size equivalent identifier, or a unit dose identifier;
assemble a second unique key by transforming the second data, wherein the second unique key comprises at least one of a package quantity identifier, a therapeutic class identifier, a clinical formulation identifier, an additional detail identifier, a package size equivalent identifier, or a unit dose identifier;
determine a relationship between the first data and the second data by comparing the first unique key and the second unique key;
analyze the relationship to create output data, wherein the output data comprises at least one of: a cost effectiveness of purchasing a drug product from different suppliers, a determination of a lowest cost per unit of the drug product, a manufacturer market share for the drug product, or a strategy for submitting a contract bid for the drug product; and
generate reports based at least partially on the output data.

2. The system of claim 1, wherein the first unique key is at least one of 25 characters, 22 characters or 18 characters in length.

3. The system of claim 1, wherein the package quantity identifier is 3 characters in length.

4. The system of claim 1, wherein the first data feed comprises national drug code data.

5. The system of claim 1, wherein the first unique key comprises a package size equivalent identifier and at least one of a package quantity identifier, a therapeutic class identifier, a clinical formulation identifier, an additional detail identifier, or a unit dose identifier.

6. A method comprising:
parsing, by a computer-based for determining relationships, a first data feed into first data;
parsing, by a computer-based system, a second data feed into second data;
assembling a first unique key by transforming the first data, wherein the first unique key comprises at least one of a package quantity identifier, a therapeutic class identifier, a clinical formulation identifier, an additional detail identifier, a package size equivalent identifier, or a unit dose identifier;
assembling, by the computer-based system, a second unique key by transforming the second data, wherein the second unique key comprises at least one of a package quantity identifier, a therapeutic class identifier, a clinical formulation identifier, an additional detail identifier, a package size equivalent identifier, or a unit dose identifier;
determining, by a computer-based system a relationship between the first data and the second data by comparing the first unique key and the second unique key; and
creating, by a computer-based system, output data by analyzing the relationship, wherein the output data comprises at least one of: a cost effectiveness of purchasing a drug product from different suppliers, a determination of a lowest cost per unit of the drug product, a manufacturer market share for the drug product, or a strategy for submitting a contract bid for the drug product.

7. The method of claim 6, wherein at the package quantity identifier is 3 characters in length.

8. The method of claim 6, wherein the first unique key is at least one of 25 characters, 22 characters or 18 characters in length.

9. The method of claim 6, wherein the first unique key comprises a package size equivalent identifier and at least one of a package quantity identifier, a therapeutic class identifier, a clinical formulation identifier, an additional detail identifier, or a unit dose identifier.

10. The method of claim 6, wherein the first unique key comprises a package quantity identifier, a therapeutic identifier, a clinical formulation identifier, a unit dose identifier and at least one of an additional detail identifier and a package size equivalent identifier.

11. The method of claim 6, wherein the output data comprises national drug code data.

12. The method of claim 6, wherein the output data is grouped according to report criteria.

13. The method of claim 12, wherein the output data is further grouped according to bid price.

14. The method of claim 6, wherein the first data feed and the second data feed are each received from at least one of a pharmaceutical supplier or a healthcare supplier.

15. A non-transitory, tangible computer-readable medium having computer-executable instructions stored thereon that, if executed by a computer, for determining g relationships, cause the computer to perform operations comprising:
parsing a first data feed into first data;
parsing a second data feed into second data;
assembling a first unique key by transforming the first data, wherein the first unique key comprises at least one of a package quantity identifier, a therapeutic class identifier, a clinical formulation identifier, an additional detail identifier, a package size equivalent identifier, or a unit dose identifier;
assembling a second unique key by transforming the second data, wherein the second unique key comprises at least one of a package quantity identifier, a therapeutic class identifier, a clinical formulation identifier, an additional detail identifier, a package size equivalent identifier, or a unit dose identifier;
determining a relationship between the first data and the second data by comparing the first unique key and the second unique key; and
creating output data by analyzing the relationship, wherein the output data comprises at least one of: a cost effectiveness of purchasing a drug product from different suppliers, a determination of a lowest cost per unit of the drug product, a manufacturer market share for the drug product, or a strategy for submitting a contract bid for the drug product.

* * * * *

UNITED STATES PATENT AND TRADEMARK OFFICE
CERTIFICATE OF CORRECTION

| | | |
|---|---|---|
| PATENT NO. | : 7,845,551 B2 | Page 1 of 1 |
| APPLICATION NO. | : 12/547796 | |
| DATED | : December 7, 2010 | |
| INVENTOR(S) | : Robert P. Helmin et al. | |

It is certified that error appears in the above-identified patent and that said Letters Patent is hereby corrected as shown below:

In Column 13 line 49, please delete "by a computer-based system" and insert therefor -- by the computer based system --.

In Column 14 line 1, please delete "by a computer-based system" and insert therefor -- by the computer based system --.

In Column 14 line 4, please delete "by a computer-based system" and insert therefor -- by the computer based system --.

In Column 14 line 37, please delete "determining g relationships" and insert therefor -- determining relationships --.

Signed and Sealed this
Eighteenth Day of January, 2011

David J. Kappos
*Director of the United States Patent and Trademark Office*